United States Patent [19]

Nesvadba et al.

[11] Patent Number: 5,750,765

[45] Date of Patent: May 12, 1998

[54] 7-SUBSTITUTED QUINONE METHIDES AS INHIBITORS FOR UNSATURATED MONOMERS

[75] Inventors: Peter Nesvadba; Samuel Evans, both of Marly, Switzerland; Matthew E. Gande, Danbury, Conn.; Volker H. von Ahn, Mahopac; Roland A. E. Winter, Armonk, both of N.Y.

[73] Assignee: Ciba Specialty Chemicals Corporation, Tarrytown, N.Y.

[21] Appl. No.: 703,763

[22] Filed: Aug. 27, 1996

Related U.S. Application Data

[62] Division of Ser. No. 422,285, Apr. 14, 1995, Pat. No. 5,583,247.

[51] Int. Cl.$^6$ .................................... C07C 69/74
[52] U.S. Cl. ................ 560/126; 560/106; 560/174; 560/231; 562/508; 558/214; 558/430; 568/377; 564/204
[58] Field of Search .................... 560/126, 174, 560/231, 106; 562/508; 558/430, 214; 568/377; 564/204

[56] References Cited

U.S. PATENT DOCUMENTS

| | | | |
|---|---|---|---|
| 4,003,800 | 1/1977 | Bacha et al. | 203/9 |
| 4,032,547 | 6/1977 | Bacha et al. | 260/396 |
| 4,040,911 | 8/1977 | Bacha et al. | 203/9 |
| 5,221,764 | 6/1993 | Roling | 560/205 |

FOREIGN PATENT DOCUMENTS

| | | |
|---|---|---|
| 0391644 | 10/1990 | European Pat. Off. . |
| 0522709 | 1/1993 | European Pat. Off. . |

OTHER PUBLICATIONS

Chemical Abstracts 1994:682461, rn=65559-25-3, Evstigneyev et al., 1992.

F.R. Hewgill et al. Aust. J. Chem. vol. 30 pp. 2565–2569 (1977).

H. Grass et al. Phosphorus, Sulfurs & Silicon vol. 47, pp. 7–13 (1990).

V.V. Ershor et al. Izv Akad. Nauk SSSR Ser. Khim v. 5 p. 928 (1966).

L. Jurd et al. J. Agric. Food Chem. vol. 27 No. 5, pp. 1007–1016, (1979).

B. Keurtek et al. Czechoslovak Aca. of Sciences vol. 6 (4) p. 305 (1976).

*Primary Examiner*—Samuel Barts
*Attorney, Agent, or Firm*—Luther A. R. Hall

[57] ABSTRACT

Ethylenically unsaturated monomers are protected from premature polymerization during manufacture and storage by the incorporation therein of an effective stabilizing amount of a 7-substituted quinone methide compound.

1 Claim, No Drawings

7-SUBSTITUTED QUINONE METHIDES AS INHIBITORS FOR UNSATURATED MONOMERS

This is a DIVISIONAL of application Ser. No. 08/422,285 filed Apr. 14, 1995 now U.S. Pat. No. 5,583,249.

The present invention relates to a compositions and a process for reducing premature polymerization of readily polymerizable unsaturated monomers during monomer manufacturing processes by incorporating therein an effective amount of a 7-aryl quinone methide compound.

BACKGROUND OF THE INVENTION

It is well known that ethylenically unsaturated monomers like vinyl aromatic compounds, such as styrene, α-methylstyrene, vinyltoluene or divinylbenzene or acrylic monomers, such as acrylic acid, methacrylic acid and their esters and amides, or unsaturated esters such as vinyl acetate or unsaturated polyesters have a strong tendency to polymerize when subjected to elevated temperatures. Manufacturing processes for such monomers typically include distillations or handling at elevated temperatures.

To prevent the premature polymerization of vinyl aromatic monomers during the distillation purification process, various compounds have been disclosed as polymerization inhibitors. These include elemental sulfur and many classes of organic chemicals having varying degrees of success in industrial use. These compounds include among others nitrated phenol derivatives, C- and N-nitroso compounds, nitroxyl derivatives, diphenylamines, hydroxylamines, quinones, quinone oximes and quinone alkide derivatives.

Known inhibitors of acrylic monomer polymerization include phenothiazine, hydroquinone monomethyl ether, and methylene blue. Phenothiazine, while unable to totally inhibit polymerization of acrylic monomers, is a commonly used co-additive. Recent patents claim phenylenediamines with soluble transition metal salts (U.S. Pat. No. 5,221,764) and aryl N-nitroso compounds (EP 0 522 709 A2) are active in acrylic monomer stabilization. However, there still remains a need for a compound to improve the stability of acrylic monomers during their distillation. The need exists for a stable polymerization inhibitor system which will effectively and safely prevent the premature polymerization of unsaturated monomers during distillation and purification processes, particularly if air is absent.

U.S. Pat. Nos. 4,003,800 and 4,040,911 disclose the use of quinone alkides in a styrene purification process. U.S. Pat. No. 4,032,547 describes the preparation of quinone methides from phenols by a persulfate oxidation process mediated by ferricyanide.

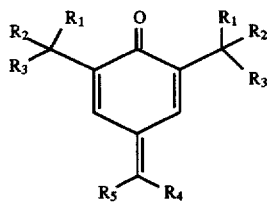

In the generic structure depicted above, groups $R_4$ and $R_5$ include phenyl and substituted phenyl, but such structures are not exemplified in U.S. Pat. No. 4,003,800 nor is any 7-aryl quinone methide derivative included among the 17 individually named compounds in U.S. Pat. No. 4,003,800. All 17 compounds have either no substituents or an alkyl substituent in the 7-position. individually named compounds in U.S. Pat. No. 4,003,800 include six with unsubstituted 7-methylene groups, which are clearly too thermally unstable for practical use as industrial polymerization inhibitors in unsaturated monomers.

There is much convincing experimental evidence proving that quinone methides unsubstituted in the 7-position, i.e. compounds with an unsubstituted exomethylene group, are in fact too unstable to be even isolated at room temperature. These methylene derivatives can be prepared only as a very dilute 10-3 to 10-5 molar solutions which are stable only few days in the absence of light (See, e.g.,: P. Gruenanger in Houben-Weyl, Methoden der Organischen Chemie, Vol. 7/3B, p. 420).

Quinone methides with 7-alkyl groups also lack thermal stability to be used efficiently in the present application.

Surprisingly, the instant group of quinone methides with electron withdrawing substituents at the 7-methylene group are not disclosed in U.S. Pat. Nos. 4,003,800; 4,040,911 and 4,032,547, are found to be much more active as polymerization inhibitors for unsaturated monomers than the quinone methides described in said U.S. patents.

DETAILED DISCLOSURE

The instant invention pertains to a composition for inhibiting the premature polymerization of an ethylenically unsaturated monomer which comprises (a) an ethylenically unsaturated monomer or mixture of monomers, and (b) an effective inhibiting amount of a compound of formula I

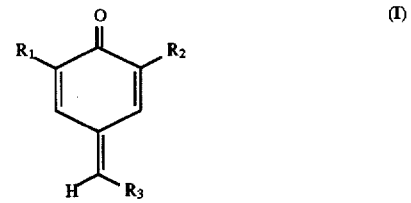

wherein $R_1$ and $R_2$ are independently alkyl of 4 to 18 carbon atoms, cycloalkyl of 5 to 12 carbon atoms or phenylalkyl of 7 to 15 carbon atoms, and $R_3$ is —CN, —COOH, —COOR$_4$, —COR$_5$, —OCOR$_6$, —CONR$_7$R$_8$ or —PO(OR$_9$)$_2$ where $R_4$ is alkyl of 1 to 18 carbon atoms, cycloalkyl of 5 to 12 carbon atoms, phenyl or benzyl, $R_5$ is alkyl of 1 to 18 carbon atoms, aryl of 6 to 10 carbon atoms or said aryl substituted by 1 or 2 alkyl of 1 to 4 carbon atoms or by hydroxyl, $R_6$ is alkyl of 1 to 18 carbon atoms, aryl of 6 to 10 carbon atoms or said aryl substituted by 1 or 2 alkyl of 1 to 4 carbon atoms or by hydroxyl, $R_7$ and $R_8$ are independently hydrogen, alkyl of 1 to 18 carbon atoms or said alkyl substituted by alkylamino of 1 to 4 carbon atoms, by dialkylamino of 2 to 8 carbon atoms or by hydroxyl; benzyl, aryl of 6 to 10 carbon atoms or said aryl substituted by alkyl of 1 to 4 carbon atoms, by alkylamino of 1 to 4 carbon atoms, by dialkylamino of 2 to 8 carbon atoms, by phenylamino or by hydroxyl, or —NR$_7$R$_8$ is morpholino, piperidino or pyrrolidino, and $R_9$ is hydrogen or alkyl of 1 to 18 carbon atoms.

Preferably, $R_1$ and $R_2$ are tert-butyl, tert-amyl, tert-octyl, cyclohexyl, α-methylbenzyl or α,α-dimethylbenzyl.

Most preferably, $R_1$ and $R_2$ are tert-butyl, tert-amyl or tert-octyl.

Preferably, $R_3$ is —CN, —COOH, —COOR$_4$, —COR$_5$, —OCOR$_6$, —CONR$_7$R8 or —PO(OR9)2 where $R_4$ is alkyl of 1 to 8 carbon atoms, $R_5$ is methyl or phenyl, $R_6$ is alkyl of 1 to 18 carbon atoms or phenyl, $R_7$ and $R_8$ are independently hydrogen or alkyl of 1 to 18 carbon atoms, or —NR$_7$R$_8$ is morpholino or piperidino, and $R_9$ is alkyl of 1 to 4 carbon atoms.

Most preferably, $R_3$ is —CN, —COOH, —COOR$_4$, —COR$_5$, —CONR$_7$R$_8$ or —PO(OR$_9$)$_2$ where $R_4$ is alkyl of 1 to 4 carbon atoms, $R_5$ is methyl or phenyl, $R_7$ and $R_8$ are independently hydrogen or alkyl of 1 to 4 carbon atoms, or —NR$_7$R$_8$ is morpholino, and $R_9$ is alkyl of 1 to 4 carbon atoms.

Preferably, the compounds of formula I are (3,5-di-tert-butyl-4-oxocyclohexa-2,5-dienylidene) acetonitrile, (3,5-di-tert-butyl-4-oxocyclohexa-2,5-dienylidene)acetic acid, (3,5-di-tert-amyl-4-oxocyclohexa-2,5-dienylidene)acetic acid, methyl (3,5-di-tert-butyl-4-oxocyclohexa-2,5-dienylidene) acetate, ethyl (3,5-di-tert-butyl-4-oxocyclohexa-2,5-dienylidene) acetate, n-butyl (3,5-di-tert-butyl-4-oxocyclohexa-2,5-dienylidene) acetate, 2,6-di-tert-butyl-4-(2-oxopropylidene)-cyclohexa-2,5-dienone, diethyl (3,5-di-tert-butyl-4-oxocyclohexa-2,5-dienylidene) methanephosphonate, (3,5-di-tert-butyl-4-oxocyclohexa-2,5-dienylidene)methyl acetate, (3,5-di-tert-butyl-4-oxocyclohexa-2,5-dienylidene)methyl pivalate, (3,5-di-tert-butyl-4-oxocyclohexa-2,5-dienylidene)methyl benzoate, and N,N-diethyl-2-(3,5-di-tert-butyl-4-oxocyclohexa-2,5-dienylidene)acetamide.

Each of the compounds within the scope of formula I are new except for the following known compounds:

a. (3,5-di-tert-butyl-4-oxocyclohexa-2,5-dienylidene) acetonite;

b. (3,5-di-tert-butyl-4-oxocyclohexa-2,5-dienylidene)acetic acid;

c. methyl (3,5-di-tert-butyl-4-oxocyclohexa-2,5-dienylidene)acetate;

d. diethyl (3,5-di-tert-butyl-4-oxocyclohexa-2,5-dienylidene)methanephosphonate;

e. (3,5-di-tert-butyl-4-oxocyclohexa-2,5-dienylidene) methyl acetate;

f. (3,5-di-tert-butyl-4-oxocyclohexa-2,5-dienylidene)methyl pivalate;

g. (3,5-di-tert-butyl-4-oxocyclohexa-2,5-dienylidene) methyl benzoate;

h. 2,6-di-tert-butyl-4-(2-oxophenylethylidene)-cyclohexa-2,5-dienone; and i. diisopropyl (3,5-di-tert-butyl-4-oxocyclohexa-2,5-dienylidene)methane-phosphonate.

The effective amount of the instant 7-substituted quinone methide polymerization inhibitor of formula I may vary over wide ranges depending upon the particular unsaturated monomer and the conditions of distillation. Preferably, the total amount of an instant quinone methide of formula I is from 1 ppm to about 2000 ppm (based upon the weight of the monomer being inhibited from premature polymerization). For most applications, the inhibitor system is used in the range of 5 to 1000 ppm. As the temperature increases, greater amounts of inhibitor are required.

Another aspect of the instant invention is the synergy observed when the instant compounds of formula I are combined with a 7-aryl quinone methide of formula II. The compounds of formula II are disclosed in a copending patent application Serial No. It has been found that the 7-substituted quinone methides according to formula I of this invention show strong synergistic effect in preventing the premature polymerization of ethylenically unsaturated monomers when combined with the 7-aryl quinone methides according to formula II. Valuable inhibition of unsaturated monomer polymerization is thus obtained using combinations of these two quinone methide classes.

Thus, this aspect of the instant invention involves a composition for inhibiting the premature polymerization of an ethylenically unsaturated monomer which comprises (a) an ethylenically unsaturated monomer or mixture of monomers, and (b) an effective inhibiting amount of a synergistic mixture of (i) at least one compound of formula I

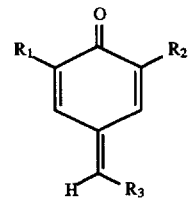

(I)

wherein $R_1$ and $R_2$ are independently alkyl of 4 to 18 carbon atoms, cycloalkyl of 5 to 12 carbon atoms or phenylalkyl of 7 to 15 carbon atoms, and $R_3$ is —CN, —COOH, —COOR$_4$, —COR$_5$, —OCOR$_6$, —CONR$_7$R$_8$ or —PO(OR$_9$)$_2$ where $R_4$ is alkyl of 1 to 18 carbon atoms, cycloalkyl of 5 to 12 carbon atoms, phenyl or benzyl, $R_5$ is alkyl of 1 to 18 carbon atoms, aryl of 6 to 10 carbon atoms or said aryl substituted by 1 or 2 alkyl of 1 to 4 carbon atoms or by hydroxyl, $R_6$ is alkyl of 1 to 18 carbon atoms, aryl of 6 to 10 carbon atoms or said aryl substituted by 1 or 2 alkyl of 1 to 4 carbon atoms or by hydroxyl, $R_7$ and $R_8$ are independently hydrogen, alkyl of 1 to 18 carbon atoms or said alkyl substituted by alkylamino of 1 to 4 carbon atoms, by dialkylamino of 2 to 8 carbon atoms or by hydroxyl; benzyl, aryl of 6 to 10 carbon atoms or said aryl substituted by alkyl of 1 to 4 carbon atoms, by alkylamino of 1 to 4 carbon atoms, by dialkylamino of 2 to 8 carbon atoms, by phenylamino or by hydroxyl, or —NR$_7$R$_8$ is morpholino, piperidino or pyrrolidino, and $R_9$ is hydrogen or alkyl of 1 to 18 carbon atoms, and (ii) at least one 7-aryl quinone methide of formula II

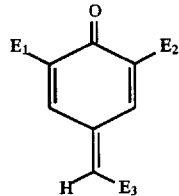

where

E$_1$ and E2 are independently alkyl of 4 to 18 carbon atoms, cycloalkyl of 5 to 12 carbon atoms or phenylalkyl of 7 to 15 carbon atoms, and E$_3$ is 2-, 3- or 4-pyridyl, 2- 3-thienyl, 2- 3-pyrryl, 2- 3-furyl, aryl of 6 to 10 carbon atoms, or said aryl substituted by one to three alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms, alkoxycarbonyl of 2 to 8 carbon atoms, hydroxy, nitro, amino, cyano, carboxy, aminocarbonyl, chloro or mixtures of said substituents.

The total amount of inhibitor (b) is in the range 1 to 2000 ppm (based on the weight of the monomer being inhibited). For most applications, the range is 5 to 1000 ppm. The relative concentrations of the compounds of formula I (i) is 5 to 95% by weight and of the compounds of formula II (ii) is 95 to 5% by weight based on the combined total weight of the component (b).

Preferably, the compounds of component I are (3,5-di-tert-butyl-4-oxocyclohexa-2,5-dienylidene) acetonitrile, (3,5-di-tert-butyl-4-oxocyclohexa-2,5-dienylidene)acetic acid, (3,5-di-tert-amyl-4-oxocyclohexa-2,5-dienylidene)acetic acid, methyl (3,5-di-tert-butyl-4-oxocyclohexa-2,5-dienylidene) acetate, ethyl (3,5-di-tert-butyl-4-oxocyclohexa-2,5-dienylidene) acetate, n-butyl (3,5-di-tert-butyl-4-oxocyclohexa-2,5-dienylidene) acetate, 2,6-di-tert-butyl-4-(2-oxopropylidene)-cyclohexa-2,5-dienone, diethyl (3,5-di-tert-butyl-4-oxocyclohexa-2,5-dienylidene) methanephosphonate, (3,5-di-tert-butyl-4-oxocyclohexa-2,5-dienylidene)methyl acetate, (3,5-di-tert-butyl-4-oxocyclohexa-2,5-dienylidene)methyl pivalate, (3,5-di-tert-butyl-4-oxocyclohexa-2,5-dienylidene)methyl benzoate, and N,N-diethyl-2-(3,5-di-tert-butyl-4-oxocyclohexa-2,5-dienylidene)acetamide.

Preferably the compounds of formula II are 2,6-di-tert-butyl-4-benzylidene-cyclohexa-2,5-dienone, 2,6-di-tert-butyl-4-(4-nitrobenzylidene)-cyclohexa-2,5-dienone, 2,6-di-tert-butyl-4-(3-nitrobenzylidene)-cyclohexa-2,5-dienone, 2,6-di-tert-butyl-4-(4-cyanobenzylidene)-cyclohexa-2,5-dienone, 2,6-di-tert-butyl-4-(4-dimethylaminobenzylidene)-cyclohexa-2,5-dienone, 2,6-di-tert-amyl-4-benzylidene-cyclohexa-2,5-dienone, 2,6-di-tert-butyl-4-(4-methoxybenzylidene)-cyclohexa-2,5-dienone, and 2,6-di-tert-butyl-4-(3,5-di-tert-butyl-4hydroxybenzylidene)-cyclohexa-2,5-dienone.

The term unsaturated monomers as used in this application includes any readily polymerizable vinyl aromatic monomer, e.g., styrene, α-methylstyrene, vinyltoluene, divinylbenzene and structural isomers, derivatives and mixtures thereof or acrylic monomer, such as acrylic acid, methacrylic acid or their esters and amides and mixtures thereof or unsaturated esters such as vinyl acetate and unsaturated polyesters and mixtures thereof.

The polymerization inhibitor compositions can be introduced into the monomer to be protected by any conventional method. It may be added as a concentrate solution in suitable solvents just upstream of the point of desired application by any suitable means. In addition, these compounds may be injected separately into the distillation train along with the incoming feed, or through separate entry points providing efficient distribution of the inhibitor composition. Since the inhibitor is gradually depleted during operation, it is generally necessary to maintain the appropriate amount of the inhibitor in the distillation apparatus by adding inhibitor during the course of the distillation process. Such addition may be carried out either on a generally continuous basis or it may consist of intermittently charging inhibitor into the distillation system if the concentration of inhibitor is to be maintained above the minimum required level.

The polymerization inhibiting compositions of this invention are also well suited for protecting the reboiler sections of a distillation column.

The following examples are meant for illustrative purposes only and are not to be construed as limiting the instant invention in any manner whatsoever.

In the Examples, styrene is used as a representative vinyl aromatic monomer and the mixture acrylic acid-octyl acrylate serves as a test monomer for acrylate monomers.

EXAMPLE 1

(3,5-Di-tert-butyl-4-oxocyclohexa-2,5-dienylidene) acetonitrile

This compound can be made by the procedure of V. V. Ershov et al., Izv. Akad. Nauk. SSSR, Ser. Khim. (5), 928 (1966) or as follows.

(A) (3,5-Di-tert-butyl-4-hydroxyphenyl)-(piperidin-1-yl)acetonitrile 48.6 g (0.2 Mol) of 3,5-di-tert-butyl-4-hydroxybenzaldehyde hemihydrate and 150 ml of heptane are azeotropically dried during 30 minutes using the Dean-Stark trap. The mixture is then cooled to about 80° C. 21.75 ml (0.22 Mol) of piperidine are added and the reflux is continued for one hour on the Dean-Stark trap. The deep yellow solution is cooled to 80° C. and 21 ml (0.23 mol) of acetone cyanohydrin are added dropwise over a period of ten minutes. The mixture is then stirred at 80° C. for another hour and then evaporated in vacuo. The oily residue is dissolved in 200 ml of ethanol and 30 ml of water and cooled under stirring to 0° C. The product is removed by filtration, washed with 120 ml of cold 80% ethanol and dried in vacuo to give 55.7 g of the intermediate product as yellow prisms, melting at 110°–111° C.

$^1$H—NMR (300 MHz, CDCl$_3$): 1.46 s (2×t-Bu), 1.40–1.55 m (CH$_2$), 1.55–1.70- m (2×CH$_2$), 2.40–2.60, m (2×CH2), 4.74 s (CH), 5.28 s (OH), 7.31 s (2ArH).

(B) (3,5-Di-tert-butyl-4-oxocyclohexa-2,5-dienylidene)acetonitrile 55.7 g (0.17 Mol) of the intermediate made in Example 1A are dissolved in 100 ml of toluene. 19 g (0.186 Mol) of acetic anhydride are added and the mixture is refluxed for one hour. The red solution is then cooled to room temperature, washed with water, 5% sodium bicarbonate and water again and evaporated in vacuo. The solid residue is recrystallized from 100 ml of hexane to give 34.5 g of the title compound as orange prisms, melting at 110°–111° C.

$^1$H—NMR (300 MHz, CDCl$_3$): 1.29 s (t-Bu), 1.32 s (t-Bu), 5.67 s (CH), 6.86 d (1ArH, J=2.5 Hz), 7.33 d (1ArH, J=2.5 Hz).

EXAMPLE 2

(3,5-Di-tert-butyl-4-oxocyclohexa-2,5-dienylidene) acetic Acid

This compound can be made by the procedure of V. V. Ershov et al. or as follows.

(A) (3,5-Di-tert-butyl-4-hydroxyphenyl)-chloroacetic Acid 309.5 g (1.5 Mol) of 2,6-di-tert-butylphenol and 266.5 g (1.8 mol) of 50% aqueous glyoxylic acid are dissolved in 1400 ml of glacial acetic acid. Then, 200 g (5.5 mol) of gazeous hydrogen chloride are introduced into this solution over a period of 2.5 hours under stirring and cooling in an ice bath to keep the temperature in the 10°–25° C. range. The mixture is then stirred at room temperature overnight, cooled to 10° C., the solid is isolated by filtration on a Buechner funnel and washed with 1000 ml water. The slightly yellow and still wet cake of the intermediate product weighs about 565 g.

(B) (3,5-Di-tert-butyl-4-oxocyclohexa-2,5-dienylidene)acetic Acid

To a cold (0° C.) solution of sodium acetate prepared from 12 g (0.3 mol) of sodium hydroxide and 17 ml (0.3 mol) of acetic acid in 75 ml of water are added 72 g of the still wet intermediate prepared in Example 2A and 50 ml of toluene. The heterogeneous mixture is then vigorously stirred for three hours while the temperature rises to room temperature. The mixture is then cooled to 0° C. again and filtered. The filter cake is washed with water and then hexane and dried to give 37 g of the title compound as orange crystals, melting at 148°–150° C.

$^1$H—NMR (300 MHz, CDCl$_3$): 1.31s (t-Bu), 1.32 s (t-Bu), 6.18 s CH), 6.82 d (1ArH, J=2.5 Hz), 8.25 d (1ArH, J=2.5 Hz)

EXAMPLE 3

(3,5-Di-tert-amyl-4-oxocyclohexa-2,5-dienylidene) acetic Acid 15.0 g (0.064 Mol) of 2,6-di-tert-amylphenol and 11.4 g (0.077 mol) of 50% aqueous glyoxylic acid are dissolved in 100 ml of acetic acid. The solution is then saturated at 15°–25° C. with hydrogen chloride gas and stirred at room temperature for additional four hours. The mixture is then poured in 400 ml of ice-water and extracted with 200 ml of ethyl acetate. The ethyl acetate layer is washed several times with water, dryed over anhydrous sodium sulfate, and evaporated in vacuo. The oily residue is then chromatographed on silica gel with ethyl acetate:hexane (1:20→1:3).

The pure fractions are recrystallized from hexane to give 6.5 g of the title compound as orange needles, melting at 109°–110° C.

$^1$H—NMR (300 MHz, CDCl$_3$): 0.65 t (CH$_3$, J=7.5 Hz), 0.67 t (CH$_3$, J=7.5 Hz), 1.23 s (CH$_3$), 1.26 s (CH$_3$), 1.810 q (CH$_2$, J=7.5 Hz), 1.812 q (CH$_2$, J=7.5 Hz), 6.17 s (CH), 6.77 d (1 ArH, J=2 Hz), 8.21 d (1 ArH, J=2 Hz).

EXAMPLE 4

Methyl (3,5-Di-tert-butyl-4-oxocyclohexa-2,5-dienylidene)acetate

This compound can be made by the procedure of F. R. Hewgill et al., Aust. J. Chem. 30, 2565 (1977) or as follows.

(A) Methyl (3,5-Di-tert-butyl-4-hydroxyphenyl) methoxyacetate 117.5 g (0.393 Mol) of the dry (3,5-di-tert-butyl-4-hydroxyphenyl)-chloroacetic acid, prepared in Example 2A, and dried at 70° C./70 mm Hg), are dissolved in 250 ml of methanol and the solution is heated under reflux. After 5–10 minutes, a white solid precipitate begins to form. The suspension is heated for additional three hours, cooled to 0° C. and filtered. The solid is washed with 100 ml of cold methanol and dried to give 109 g of the title compound as white crystals, melting at 132°–133° C.

$^1$H—NMR (300 MHz, CDCl$_3$): 1.44 s (2×t-Bu), 3.41 s (CH$_3$O), 3.75 s (CH3O), 4.69 s (CH), 5.28 s (OH), 7.21 s (2 ArH).

(B) Methyl (3,5-Di-tert-butyl-4-oxocyclohexa-2,5-dienylidene)acetate 61.6 g (0.2 Mol) of the intermediate made in Example 4A and 5.0 g of a dried FULCAT® 22B catalyst are heated in 100 ml of n-octane under reflux on a Dean-Stark liquid separator. The evolution of methanol stops after about one hour. The catalyst is then removed by filtration while still warm, and the filtrate is cooled under stirring to 0° C. The suspension is filtered to give 43 g of the title compound as orange crystals, melting at 87°–89° C.

$^1$H—NMR (500 MHz, CDCl$_3$): 1.28 s (t-Bu), 1.31 s (t-Bu), 3.81 s (CH$_3$O), 6.15 s (1 H), 6.78 d (1 ArH, J=2 Hz), 8.30 (1 ArH, J=2 Hz).

EXAMPLE 5

Ethyl (3,5-Di-tert-butyl-4-oxocyclohexa-2,5-dienylidene)acetate 65 g of still wet (3,5-di-tert-butyl-4-hydroxy-phenyl)-chloroacetic acid are prepared from 41.2 g (0.2 mol) of 2,6-di-tert-butylphenol, 35.4 g (0.24 mol) of 50% aqueous glyoxylic acid and 44 g of hydrogen chloride in 200 ml of acetic acid as described in Example 2A. This acid is dissolved in 200 ml of absolute ethanol and allowed to stand overnight. The solvent is then evaporated in vacuo, 1.0 g of p-toluenesulfonic acid is added, followed by another 200 ml of absolute ethanol. The mixture is then heated for three hours, and the ethanol is then evaporated. The residue is then stirred at 0.1 mm Hg vacuum with the bath temperature slowly increasing up to 180° C. The title compound distills at a temperature between about 140°–160° C. as a viscous orange liquid in a yield of 27 g.

$^1$H—NMR (300 MHz, CDCl$_3$): 1.28 s (t-Bu), 1.32 s (t-Bu), 1.33 q (CH3, J=6.9 Hz), 4.27 q (CH$_2$, J=6.9 Hz), 6.15 s (1H), 6.79 d (1ArH, J=2.2 Hz), 8.29 d (1 ArH, J=2.2 Hz).

EXAMPLE 6 n-Butyl (3,5-Di-tert-butyl-4-oxocyclohexa-2,5-dienylidene)acetate 68 g of still wet (3,5-di-tert-butyl-4-hydroxy-phenyl)-chloroacetic acid are prepared from 41.2 g (0.2 mol) of 2,6-di-tert-butyl-phenol, 35.4 g (0.24 mol) of 50% aqueous glyoxylic acid and 54 g of hydrogen chloride in 200 ml of acetic acid as described in Example 2 A. This acid is dissolved in 200 ml of absolute n-butanol and allowed to stand for three days. 25 ml of toluene are then added and the mixture is heated on the Dean-Stark trap for three hours. The solvents are then evaporated in vacuo to give 72.4 g of the crude n-butyl (3,5-di-tert-butyl-4-hydroxy-phenyl)-n-butoxyacetate as a slightly yellow viscous oil. 40.5 g (0.1 Mol) of this intermediate ester and 1.0 g of a dried FUL-CAT® 22B catalyst are stirred at 0.1 mm Hg vacuum with bath temperature slowly increasing up to 200° C. The title compound distills over between about 150°–170° C. as a viscous orange liquid in a yield of 24 g.

$^1$H—NMR (300 MHz, CDCl3): 0.96 t (CH$_3$, J=7.5 Hz), 1.27 s (t-Bu), 1.30 s (t-Bu), 1.38–1.48 m (CH2), 1.62–1.74 m (CH$_2$), 4.21 q (CH$_2$, J=6.5 Hz), 6.16 s (1H), 6.79 d (1 ArH, J=2.5Hz), 8.29 d (1 ArH, J=2.5Hz).

EXAMPLE 7

2,6-Di-tert-butyl-4-(2-oxopropylidene)-cyclohexa-2,5-dienone 4.12 g (0.02 Mol) of 2,6-di-tert-butylphenol and 4.0 g (0.022 mol) of 40% aqueous pyruvic aldehyde are dissolved in 20 ml of acetic acid. The solution is then saturated at 15°–25° C. with hydrogen chloride gas and stirred at room temperature for additional two hours. The mixture is then diluted with 200 ml of toluene, washed several times with water, dried over anhydrous sodium sulfate, and evaporated in vacuo. The oily residue is then chromatographed on silica gel with toluene. The pure fractions are recrystallized three times from methanol to give 0.15 g of the title compound as orange needles, melting at 70°–72° C.

$^1$H—NMR (300 MHz, CDCl$_3$): 1.42 s (t-Bu), 1.44 s (t-Bu), 1.85 s (CH$_3$), 5.65 s (CH), 6.48 dd (1 ArH, J=2.3 Hz, J'=0.5 Hz), 8.56 dd (1 ArH, J=2.3 Hz, J'=0.5 Hz).

EXAMPLE 8

Diethyl (3,5-Di-tert-butyl-4-oxocyclohexa-2,5-dienylidene)methanephosphonate This compound is prepared according to the procedure of H. Gross et al., Phosphorus, Sulfur and Silicon, 47, 7 (1990).

EXAMPLE 9

(3,5-Di-tert-butyl-4-oxocyclohexa-2,5-dienylidene) methyl Acetate

This compound is prepared according to the procedure of K. Ley, Angew. Chem., 70, 74 (1958).

EXAMPLE 10

(3,5-Di-tert-butyl-4-oxocyclohexa-2,5-dienylidene) methyl Pivalate

This compound is prepared according to the process described in EP 391,644 A2.

EXAMPLE 11

(3,5-Di-tert-butyl-4-oxocyclohexa-2,5-dienylidene) methyl Benzoate

This compound is prepared according to the procedure of K. Ley, Angew. Chem., 70, 74 (1958).

EXAMPLE 12

N,N-Diethyl-2-(3,5-di-tert-butyl-4-oxocyclohexa-2,5-dienylidene)acetamide (A) N,N-Diethyl-2-(3,5-di-tert-butyl-4-hydroxyphenyl)acetamide 7.92 g (0.03 Mol) of (3,5-di-tert-butyl-4-hydroxyphenyl) acetic acid are stirred overnight in 40 ml of heptane and 20 ml of dichloromethane with 4 ml of thionyl chloride and 4 drops of N,N-dimethylformamide. An additional 90 ml of heptane are added and then 90 ml of solvent and the excess amount of thionyl chloride are distilled off. The residual solution is cooled to room temperature and then 7.5 ml (0.072 mol) of diethylamine are added dropwise. The mixture is stirred one hour, then washed with water, 5% hydrochloric acid and water again. The solvent is evaporated in vacuo, and the residue is crystallized twice from acetonitrile to give 6.5 g of the intermediate product as colorless needles, melting at 111°–113° C.

$^1$H—NMR (300 MHz, CDCl$_3$): 1.09 t (CH3, J=7.4 Hz), 1.15 t (CH$_3$, J=7.4 Hz), 1.43 s (2xt-Bu), 3.32 q (CH$_2$, J=7.4 Hz), 3.40 q (CH2, J=7.4 Hz), 3.62 s (CH$_2$), 5.11 s (OH), 7.03 s (2ArH).

(B) N,N-Diethyl-2-(3,5-di-tert-butyl-4-oxocyclohexa-2,5-dienylidene)acetamide 4.80 g (0.015 Mol) of N,N-diethyl-2-(3,5-di-tert-butyl-4-hydroxy-phenyl)acetamide are dissolved in 60 ml of dichloromethane. To this solution a solution of 15 g (0.046 mol) of potassium hexacyanoferrate (III) and 6.0 g (0.11 mol) of potassium hydroxide in 120 ml of water is added, and the mixture is stirred one hour at room temperature under nitrogen. The organic layer is separated, washed with water and evaporated in vacuo. The solid residue is recrystallized from acetonitrile to give 3.6 g of the title compound as yellow needles, melting at 109°–110° C.

$^1$H—NMR (300 MHz, CDCl$_3$): 1.21 t (CH$_3$, J=7.4 Hz), 1.22 t (CH$_3$, J=7.4 Hz), 1.28 s (t-Bu), 1.29 s (t-Bu), 3.39 q (CH$_2$, J=7.4 Hz), 3.51 q (CH$_2$, J=7.4 Hz), 6.49 s (CH), 6.83 d (1ArH, J=2.5 Hz), 7.55 d (1ArH, J=2.5 Hz).

EXAMPLE 13

Inhibition of Styrene Monomer (A) Series of 7-substituted quinone methides

Commercial grade styrene is freed of tert-butyl catechol storage stabilizer by washing with 1N sodium hydroxide, water and subsequent distillation under reduced pressure. A 300 mL 3-necked flask equipped with thermometer, condenser, rubber septum and magnetic stirrer bar is charged with 100 g of purified styrene and 20.0 mg of experimental inhibitor or 20 mg of a mixture of inhibitors, yielding styrene with 200 ppm of total inhibitors. An oxygen-free atmosphere is established by five consecutive evacuations and backfilling with nitrogen, followed by sparging the styrene solution with pure nitrogen for 15 minutes. The vessel is then immersed into a mechanically stirred and thermostatically controlled oilbath at 120° C. and heated for 45 minutes. The amount of polystyrene formed is then determined by refractive index measurements, calibrated with authentic polystyrene in styrene solutions of known concentration. Without any added inhibitor 6.2% polystyrene is formed. Polymer levels obtained with inhibitors are listed in the table below.

| Compound of Example | Percent Polymer after 45 Minutes |
| --- | --- |
| None | 6.2 |
| 1 | 0.0 |
| 2 | 0.0 |
| 3 | 0.0 |
| 4 | 0.0 |
| 5 | 0.0 |
| 6 | 0.0 |
| 7 | 0.0 |
| 9 | 0.16 |
| 10 | 0.16 |
| 11 | 0.16 |
| 12 | 0.32 |

Each of these 7-substituted quinone methides is quite effective as a polymerization inhibitor for styrene monomer.

Comparison of the instant 7-substituted quinone methides with quinone methides of the prior art (U.S. Pat. No. 4,003,800)

Following the procedure described in Example 13, Part (A) the percent polymer after 45 minutes is recorded in the table below where the inhibitor (at 200 ppm) is an instant compound or a closely related prior art quinone methide.

| Compound of Example | Percent Polymer after 45 Minutes |
| --- | --- |
| None | 6.2 |
| 1 | 0.0 |
| 2 | 0.0 |
| 4 | 0.0 |
| A* | 0.16 |
| B* | 1.13 |
| C* | 3.23 |

*A is 2,6-di-tert-butyl-4-ethylidene-cyclohexa-2,5-dienone.
*B is 2,6-di-tert-butyl-4-isobutylidene-cyclohexa-2,5-dienone.
*C is 2,6-di-tert-butyl-4-tert-amylidene-cyclohexa-2,5-dienone.

These data clearly show that the instant 7-substituted quinone methides provide much better inhibition of polymerization of styrene than the compounds described in U.S. Pat. No. 4,003,800. Indeed, with the instant 7-substituted quinone methides, no polymer is detected after 45 minutes, whereas with the prior art compounds of U.S. Pat. No. 4,003,800 substantial amounts of polymer are formed during the same time period.

(C) Effect of Oxygen

The influence of oxygen on the styrene polymer formation is demonstrated with cyano compound of Example 1. In the presence of 0.66% oxygen, no polymer formed after 45 minutes. This is the same result found under pure nitrogen.

(D) Synergy with 7-aryl quinone methides

Blends of 7-aryl quinone methides with 7-substituted quinone methides of this invention are found to be considerably more effective at reducing the amount of polymer formed than is either component by itself at the same total inhibitor concentration. This synergistic effect is demonstrated in the table below for the mixture of 2,6-di-tert-butyl-4-benzylidene-cyclo-2,5-dienone (Compound D) and (3,5-di-tert-butyl-4-oxocyclohexa-2,5-dienylidene)acetonitrile (compound of Example 1).

| Compound of Example | Conc.(ppm) | Percent Polymer after 150 Minutes |
| --- | --- | --- |
| 1 | 200 | 2.90 |
| D | 200 | 2.26 |
| 1 plus | 100 | |
| D | 100 | 1.61 |

EXAMPLE 14

Inhibition of Acrylates

A screening test to test the radical polymerization inhibitors for acrylate monomers involves the radical induced polymerization of a 3:1 mixture of acrylic acid and octyl acrylate in a low molecular weight carboxylic acid solvent. Free radicals are generated by the thermal decomposition of azo-bis-isobutyronitrile (AIBN) at 60° C. The degree of polymerization is determined by periodically measuring the solution viscosity, and comparing it to the initial viscosity. A four-fold increase in viscosity is considered failure. Induction periods are determined by measuring the time before a significant change in viscosity is observed.

Unless otherwise noted, all reagents and solvents are used as received. A solution of acrylate (3:1 weight ratio of acrylic acid to octyl acrylate) in propionic acid (0.1 g/mL) containing AIBN (recrystallized from methanol) and the inhibitor additive to be tested (2% and 400 ppm, respectively, with respect to acrylate) is prepared. To a Canon-Fenske viscometer is added 10 mL of the test solution, which is then purged with either nitrogen (>99.995%) or an oxygen gas mixture (6500 ppm oxygen in nitrogen) for five minutes before being heated in a 60° C. oil bath. After an additional purge for five minutes, drop times are automatically measured (10 minute intervals, with a one minute gas purge before each measurement) using a Design Scientific automated viscometer and a custom software package. The results are summarized in the table below.

| Inhibitor of Example (400 ppm) | Induction Period (min) | 4-Fold Viscosity Increase (min) |
| --- | --- | --- |
| Nitrogen | | |
| None | 0 | 45 |
| 1 | 45 | 80 |
| 2 | 35 | 67 |
| 4 | 40 | 78 |
| 6500 ppm Oxygen in Nitrogen | | |
| None | 0 | 102 |
| 1 | 75 | 134 |
| 2 | 65 | 129 |
| 4 | 75 | 160 |

It is clear from the data given in the table above that the instant compounds are very effective acrylate monomer inhibitors under either nitrogen or oxygen.

What is claimed is:

1. A compound of formula I

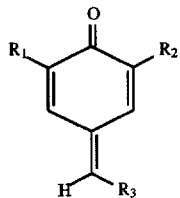 (I)

wherein

R₁ and R₂ are independently alkyl of 4 to 18 carbon atoms, cycloalkyl of 5 to 12 carbon atoms or phenylalkyl of 7 to 15 carbon atoms, and R₃ is —CN, —COOH, —COOR₄, —COR₅, —OCOR₆, —CONR₇R₈ or —PO(OR₉)₂ where R₄ is alkyl of 1 to 18 carbon atoms, cycloalkyl of 5 to 12 carbon atoms, phenyl or benzyl, R₅ is alkyl of 1 to 18 carbon atoms, aryl of 6 to 10 carbon atoms or said aryl substituted by 1 or 2 alkyl of 1 to 4 carbon atoms or by hydroxyl, R₆ is alkyl of 1 to 18 carbon atoms, aryl of 6 to 10 carbon atoms or said aryl substituted by 1 or 2 alkyl of 1 to 4 carbon atoms or by hydroxyl, R₇ and R₈ are independently hydrogen, alkyl of 1 to 18 carbon atoms or said alkyl substituted by alkylamino of 1 to 4 carbon atoms, by dialkylamino of 2 to 8 carbon atoms or by hydroxyl; benzyl, aryl of 6 to 10 carbon atoms or said aryl substituted by alkyl of 1 to 4 carbon atoms, by alkylamino of 1 to 4 carbon atoms, by dialkylamino of 2 to 8 carbon atoms, by phenylamino or by hydroxyl, or —NR₇R₈ is morpholino, piperidino or pyrrolidino, and R₉ is hydrogen or alkyl of 1 to 18 carbon atoms, but excluding a. (3,5-di-tert-butyl-4-oxocyclohexa-2,5-dienylidene) acetonitrile;

b. (3,5-di-tert-butyl-4-oxocyclohexa-2,5-dienylidene) acetic acid;

c. methyl (3,5-di-tert-butyl-4-oxocyclohexa-2,5-dienylidene)acetate;

d. diethyl (3,5-di-tert-butyl-4-oxocyclohexa-2,5-dienylidene)methanephosphonate;

e. (3,5-di-tert-butyl-4-oxocyclohexa-2,5-dienylidene) methyl acetate;

f. (3,5-di-tert-butyl-4-oxocyclohexa-2,5-dienylidene) methyl pivalate;

g. (3,5-di-tert-butyl-4-oxocyclohexa-2,5-dienylidene) methyl benzoate;

h. 2,6-di-tert-butyl-4-(2-oxophenylethylidene)-cyclohexa-2,5-dienone; and i. diisopropyl (3,5-di-tert-butyl-4-oxocyclohexa-2,5-dienylidene)methane-phosphonate.

* * * * *